United States Patent [19]

Kilbourne

[11] 4,009,258

[45] Feb. 22, 1977

[54] INFLUENZA VACCINE CONTAINING A RECOMBINANT, ANTIGENICALLY HYBRIDIZED VIRUS AND METHOD OF USING THE SAME

[75] Inventor: Edwin D. Kilbourne, Ridgewood, N.J.

[73] Assignee: The Mount Sinai School of Medicine of the City University of New York, New York, N.Y.

[22] Filed: Aug. 5, 1974

[21] Appl. No.: 494,716

Related U.S. Application Data

[63] Continuation of Ser. No. 291,797, Sept. 25, 1972, abandoned.

[52] U.S. Cl. .................................. 424/89; 195/1.1; 195/1.2; 195/1.8

[51] Int. Cl.$^2$ ................... A61K 39/12; C12K 5/00; C12K 7/00

[58] Field of Search ................ 424/89; 195/1.1, 1.2

[56] References Cited

OTHER PUBLICATIONS

Kilbourne–Science, vol. 160, Apr. 1968, pp. 74 and 75.

Schulman et al.–Proc. National Acad. of Science–vol. 63, No. 2, pp. 326–333.

*Primary Examiner*—Sam Rosen
*Attorney, Agent, or Firm*—Brumbaugh, Graves, Donohue & Raymond

[57] ABSTRACT

An influenza vaccine is disclosed which comprises, as an active ingredient, a recombinant, antigenically hydridized virus which has a hemagglutinin antigen that has substantially no cross-reactivity with those influenza viruses against which the vaccine is to be effective and a neuraminidase antigen which has substantial cross-reactivity with the influenza viruses against which the vaccine is to be effective. The neuraminidase can be derived from a virus antigenically representative of the contemporary or prevalent influenza virus of interest, e.g., H3N3, the Hong Kong variant of influenza, while the hemagglutinin antigen, in a preferred embodiment of the invention, is obtained from A-1/equine virus or from other influenza viruses of other antigenic subtypes, such as HON1 or H1N1.

8 Claims, No Drawings

INFLUENZA VACCINE CONTAINING A RECOMBINANT, ANTIGENICALLY HYBRIDIZED VIRUS AND METHOD OF USING THE SAME

This application is a continuation of my earlier application Ser. No. 291,797 filed Sept. 25, 1972, now abandoned.

The present invention is directed to an influenza vaccine, a recombinant, antigenically hybridized virus which forms the active component thereof, and a method of immunization using the vaccine.

The prior art has relied exclusively upon vaccines which comprise, as an active component, viruses containing hemagglutinin and neuraminidase antigens which both have a substantial cross-reactivity with the type of virus against which the vaccine is to be effective. The term "cross-reactivity" as used herein refers to the ability of a given virus to produce antibodies which will inhibit challenge by another virus. When prior art vaccines are administered to an animal they produce antibodies in the animal which are effective against both surface antigens of the wild influenza virus. The use of such a vaccine protects the host animal against both infection and manifestation of symptoms of illness. However, the protection afforded when such prior art vaccines are used in quite transient for reasons that are not entirely clear to persons of skill in the art.

Various recombinant viruses are known and have been used as laboratory reagents to analyze human and animal sera for their antibody content. In addition, recombinant viruses which contain hemagglutinin and neuraminidase antigens which both have substantial cross-reactivity with the influenza virus which subsequently challenges immunity have been used to immunize animals, such as man, swine, horses and fowl. Schulman et al., *Proceedings of the National Academy of Sciences*, Vol. 63, No. 2, pp. 326–333 (June 1969), "Correlated Studies of a Recombinant Influenza Virus Vaccine", *The Journal of Infectious Diseases*, Vol. 124, No. 5 (1971), and *The New York Times*, Aug. 13, 1972. Although it has been stated that some evidence had been obtained which was consistent with the possibility that a certain type of neuraminidase is the sole antigenically functional component of a particular recombinant virus, Laver et al., *Virology*, Vol. 30, p. 500 (1966), it has not been recognized heretofore that long-term protection against influenza virus can be obtained by using, in a suitable influenza vaccine, a recombinant, antigenically hybridized virus containing a hemagglutinin antigen having substantially no cross-reactivity with the influenza virus against which the animal is to be protected and a neuraminidase antigen having substantial cross-reactivity with that particular influenza virus of interest. The use of such a monorather than bi-specific virus in the vaccine allows the animal to become infected with the wild influenza virus with which it is challenged while protecting it against manifestations or symptoms of illness. The presence of such infection in the animal is believed to stimulate the natural immunological response of that animal thereby aiding in giving long-term protection.

The present invention is an influenza vaccine which comprises, as an active ingredient thereof, a recombinant, antigenically hybridized virus which contains a hemagglutinin antigen having substantially no cross-reactivity with the challenge influenza virus against which the vaccine is to protect the host animal and a neuraminidase antigen which has substantial cross-reactivity with the challenge influenza virus against which the vaccine is to be effective. When such a vaccine is administered only antibodies to the neuraminidase, but not the hemagglutinin, of the challenge virus are produced in any substantial amounts. Immunization of the host animal, or man which is subject to naturally occurring influenza, is performed by administering an effective amount of the vaccine containing the recombinant, antigenically hybridized virus by any suitable route of administration, e.g., by intraperitoneal, subcutaneous or intramuscular injection. Also forming a part of the present invention is a recombinant, antigenically hybridized virus derived from parental viruses which are non-neurovirulent and which contains a hemagglutinin antigen having substantially no cross-reactivity with contemporary human influenza viruses and a neuraminidase antigen which does have such substantial cross-reactivity.

The process for preparing the recombinant, antigenically hybridized virus and vaccine thereof of the present invention is described by Kilbourne, *Hospital Practice*, October 1971, pp.103–106 and 111–114. It basically involves recombination and hybridization of two viral parents to produce hybrid recombinant progeny having some of the antigenic characteristics of both parents. It is essential that the ultimate progeny of the hybridization procedure contain a neuraminidase antigen which has substantial cross-reactivity with the type of virus against which the vaccine is to be effective, and a hemagglutinin surface antigen having substantially no cross-reactivity with such virus.

A variety of possible viruses can be used in forming the recombinant virus depending upon the particular strain or strains of influenza virus against which the vaccine is to be effective. It is possible to use quite a few subtype viruses of Type A, B or C influenza viruses. The H0N1 and H1N1 subtypes, for example, are described in *Bull, W.H.O.*: 45, 119 (1971). For example, one of the viral parents used in the recombination step can be an influenza virus selected from influenza A subtypes including H0N1, H1N1, H2N2 or H3N2 viruses. One particular virus of great importance at the present time in immunization work is the Hong Kong (HK) variant of influenza which is sometimes designated as the A/Hong Kong (H3N2) influenza virus.

A recombinant virus according to the present invention which is effective against the Hong Kong variant can be formulated by recombining an A. influenza virus, e.g. A/PR8/34 (H0N1), with the Hong Kong variant, e.g., HK/Aichi/68, (H3N2) to form hybrid recombinants, some of which contain hemagglutinin and neuraminidase antigens which both have cross-reactivity with the type of influenza virus against which the vaccine is to be effective. This portion of the population of the first progeny, e.g., H3N2, is then recombined after isolation with another virus which has a hemagglutinin antigen having substantially no cross-reactivity with the influenza virus against which the vaccine is to be effective. One typical virus which can be used to supply this non cross-reactive hemagglutinin antigen is A/eql/56 (Heq$_1$ Neq$_1$) virus. The resulting progeny of this second recombination step includes a recombinant, antigenically hybridized virus containing a hemagglutinin antigen from the A/eql virus and a neuraminidase antigen from the Hong Kong variant of influenza virus. Such a virus, after isolation, when used as an active component in a virus vaccine, will protect the host animal against the Hong Kong variant of influenza. If the vaccine is desired for use in man, the parent strains used in the recombination steps should be non-neurovirulent. The absence of neurovirulence in such viruses is indicated by the inability of the viruses to produce plaques or virus colonies in a human conjunctival cell-culture system (e.g., clone 1-5C-4 cells, as described in Suguira et al., *Virology*, Vol. 26, 478–488 [1965]).

The process used in the formation of recombinant viruses is a known procedure in the art and is described in a number of publications including the following: Kilbourne and Murphy, *J. Exper. Med.:* 111, 387 (1960); *Science*, Vol. 160, April 5, 1968, pp. 74–75; and Laver and Kilbourne, *Virology*, Vol. 30, pp. 493–501 (1966). It basically comprises inoculating chick embryo allantoic sacs with the two viruses which are to be recombined. The resultant hybrid progeny are hybrids of both parental viruses. Generally, a high yield, i.e., high growth potential, and a low yield virus will be used as parents. A portion of the hybridized progeny of the recombination step can be eliminated in a cloning step by adding an antibody which is specifically cross-reactive with the virus hybrids of the undesired serotype. The remaining hybrid progeny are then, if necessary, inoculated into further chick embryo allantoic sacs, and when removed, contain a higher percentage of the progeny of desired serotype. Diluting the viruses to high dilution values insures that the high yield virus progeny will outgrow those having the lower growth potential.

A suitable vaccine is prepared by adding from about 500 to about 2,000 chick cell agglutinating (CCA) units or its equivalent, e.g. in hemagglutination titer (HA), of the recombinant, antigenically hybridized virus to 1 ml of buffered saline, either with or without the presence of a mineral oil adjuvant. The recommended dosage for injection of the vaccine of the present invention into man is from 500 to 1000 CCA units or its equivalent. The CCA test measures the hemagglutinating activity of vaccines being tested with a reference vaccine and is described by Tauraso et al., *Bull. W.H.O.*, Vol. 41, 497–506 (1969) and Hennessy, *Bull. W.H.O.*, Vol. 41, 553 (1969). In general, the hemagglutination observed is the direct agglutination of erythrocytes by influenza virus.

The present invention is further illustrated by the following examples:

EXAMPLE I

To produce the antigenically hybridized, recombinant virus used in the present invention, groups of 11-day old chick embryos (four per group) were inoculated with $10^4$ $EID_{50}$ of the H3N2 recombinant* and A/eql influenza virus. After a forty hour incubation period, allantoic fluids were harvested. These fluids were then passed individually at 1:10 dilution with a 1:10 dilution of antiserum to a H3N1 recombinant virus to selectively inhibit the H3N2 parental virus and to isolate an antigenically hybrid virus which is HeqlN2. Following two such passages with antiserum, the control parallel passage group of H3N2 recombinant virus alone was found to be negative for virus by the hemagglutination test. By inference, it was then judged that the recombinational group (in which hemagglutinating virus was detected) contained virus unlike the parental strains. Allantoic fluids from eggs in the recombinational group were then passed at limiting dilutions again with H3N1 antiserum. One fluid was found to be positive at a dilution of $10^{-8}$. This virus contained neuraminidase inhibited by H3N2 antiserum and the hemagglutinin of the virus was determined to be indistinguishable from that of the parent A/eql. Thus, a recombinant, antigenically hybridized virus was obtained. It can be represented as H/eql/N2 and is derived from the hemagglutinin antigen from the parent eql virus and the neuraminidase antigen from H3N2.

* This recombinant was formed by recombination of A/PR8/Ann Arbor/34(H0N1) and A/Aichi/68 (H3N2). Both these strains and the recombinant formed therefrom are used in commercial vaccine production in the United States. All are bi-specific rather than monospecific viruses. If desired, wild type Hong Kong virus could have been used as the neuraminidase donor rather than the H3N2 recombinant.

EXAMPLE II

A vaccine was produced containing the recombinant antigenically hybridized virus produced in Example I by inoculating chick embryo allantoic sacs with the diluted virus and harvesting the allantoic fluid after a two-day growth period. The allantoic fluid was preliminarily purified by low speed centrifugation which was followed thereafter by zonal ultracentrafugation of semi-purified allantoic fluid virus. A product consisting chiefly of spherical forms of the virus which had a hemagglutination titer of 1:3072 per 0.1 ml. This virus was inactivated by formalin by standard procedures. It was then tested for the presence of extraneous or uniactivated virus by injection of mice according to conventional techniques as required by the Division of Biologic Standards of the Food and Drug Administration.

EXAMPLE III

Preliminary antigenicity studies in human volunteers were carried out using the vaccine produced in Example II. Each of four volunteers received 500 CCA units of the vaccine in a 1 ml dose administered in a single subcutaneous injection. Whole blood for serum was taken just before vaccination (Sample No. 1) and twenty-eight days later (Sample No. 2) for study of specific antibody response to the vaccine. The results are given below:

|  | Table | Titer NI* | PSR** |
|---|---|---|---|
| Volunteer 1 | Sample No. 1 | <10 | <400 |
|  | Sample No. 2 | 40 | 1600 |
| Volunteer 2 | Sample No. 1 | <10 | <400 |
|  | Sample No. 2 | 40 | 1600 |
| Volunteer 3 | Sample No. 1 | <10 | <400 |
|  | Sample No. 2 | 20 | 800 |
| Volunteer 4 | Sample No. 1 | <10 | <400 |
|  | Sample No. 2 | 160 | 3200 |

*Neuraminidase-inhibition titrations. This test is described by Kilbourne et al., J. Inf. Diseases, Vol. 124, No. 5, p. 451 (November 1971) and Aminoff, Biochem. J., Vol. 81, 384–392 (1961). The values shown are reciprocals of the dilution of antiserum causing a 50% reduction of enzymatic activity.

**Plaque size reduction titer. This test is described in Jahiel et al., J. Bacteriol., Vol. 92, pp. 1521–1534, and is a measure of the reduction noted in virus colonies when treated with antiserum. It also is expressed as a reciprocal of the dilution of antiserum causing a 50% decrease in median plaque radius and plaques per plate. The PSR is specifically mediated through reaction of antiserum with the neuraminidase component of the influenza virus (Kilbourne et al. J. Virol.: 2, 281 [1968]).

mediated through reaction of antiserum with the neuraminidase component of the influenza virus (Kilbourne et al. *J. Virol.*: 2, 281 [1968]).

EXAMPLE IV

Rabbits were immunized with the vaccine produced in Example II with graded doses of diluted vaccine at 0, 29, 42 and 49 days, respectively.

| Rabbit | Vaccine Dilution | Immunization (Days) | NI | PSR | HI* |
|---|---|---|---|---|---|
| 1 | 1:2 | 0 | <2 | 400 | 20 |
|   |     | 29 | — | <400 | — |
|   |     | 42 | <2 | <400 | 20 |
|   |     | 49** | 10 | 1600 | 2560 |
| 2 | 1:2 | 0 | <2 | <400 | <10 |
|   |     | 29 | — | 400 | — |
|   |     | 42 | 2 | 400 | 320 |
|   |     | 49 | 50 | 3200 | 5120 |
| 3 | 1:8 | 0 | <2 | <400 | <10 |
|   |     | 29 | — | 400 | — |
|   |     | 42 | 2 | 400 | 80 |
|   |     | 49 | 10 | 800 | 1280 |
| 4 | 1:8 | 0 | <2 | <400 | <10 |
|   |     | 29 | — | 400 | — |
|   |     | 42 | 2 | 400 | 160 |
|   |     | 49 | 10 | 1600 | 2560 |
| 5 | 1:32 | 0 | <2 | <400 | <10 |
|   |      | 29 | — | <400 | — |
|   |      | 42 | 2 | 400 | <10 |
|   |      | 49 | 10 | 800 | 80 |

*Hemagglutination-inhibiting titer. The test was preformed by the microtiter technique described by Sever, *J. Immun.*, Vol. 88, 320–29 (1962).
**Post-booster; 2nd injection given at 42 days.

The $AD_{50}$ (minimal antigenic dose) titer of the vaccine was >32 (NI) and 32 (PSR). It is the estimated dilution of vaccine which will elicit antibody response in 50% of the animals.

EXAMPLE V

Mice were immunized according to the procedure described in Schulman & Kilbourne, *J. Infectious Diseases*, 124, No. 5, pp. 468–470 (Nov. 1971). Groups of mice were injected intraperitoneally with 0.2 ml of the same graded five-fold dilutions of Heql/N2, the active component of the vaccine of this invention, and with an influenza B-virus vaccine (control vaccine) of comparable titer, Kilbourne et al., *J. Infect. Dis.*: 124, 449–472 (1971). Six weeks later, five mice in each group were bled to obtain specimens of serum. The results of HI and NI titers are given below. Ten animals in each group were challenged by exposure to aerosols of graded dilutions of Aichi virus, i.e. H3N2 (Hong Kong) influenza virus, and were autopsied 48 hours later to determine the proportion of mice in each group infected with each virus concentration (aerosol MID 50). The remaining animals were challenged by exposure to an aerosol of a single concentration of mouse-adapted Aichi virus. Pulmonary viral titers were measured in five animals in each group, three days after challenge, and pulmonary lesions were assessed seven days after challenge in five others. The results are given in the following table:

| Vaccine | Post-immunization antibody | | Post-challenge (H3N2) | | | |
|---|---|---|---|---|---|---|
|  | HI | NI | lesions % ++ | Pulmonary virus titer +++ | HI | NI |
| Heql/N2 | <1.0* | 1.0(5/5) | 5 | 5.9 | 3.3+ | 7.0** |
| Control | <1.0 | <1.0 | 65 | 6.6 | 3.3 | 2.6 |

*vs H3N2 (log 2 of reciprocal of arithmetic dilution and endpoint)
**vs HON2
+vs H3N1
++Extent of lung lesions (5), five animals in each group.
+++Numbers given are $\log_{10}$ of 50% egg infectious doses; geometric mean of individual titrations of five animals.
5/5 - all of 5/5 animals sampled had NI antibody
HI - hemagglutinin-inhibition
NI - neuraminidase-inhibition

EXAMPLE VI

Human volunteers were administered 1 ml subcutaneous or intramuscular injections of about 500–600 CCA units of the vaccine of the present invention. The three tables given below summarize the results. The test procedure employed is described in Leibowitz et al. *J. Infect. Diseases:* 124, No. 5, pp. 481–486 (Nov. 1971). The controls received influenza B virus vaccine of comparable CCA titer:

TABLE I

Serologic Response to Immunization with Heql/N2 and Control Vaccines.

Table I

| Vaccine Group | Serologic Response to Immunization with Heq1/N2 and Control Vaccines. | | | | | | |
|---|---|---|---|---|---|---|---|
|  |  | Anti-HA(neutralization) Response to H3N1 | Neuraminidase-inhibition (NI) Response to HON2 | | | | |
|  |  |  |  | Post-immunization day** | | | |
|  | No. | | No. Responding | 0 | 36 | 45 | 58 |
| Control | 13 | 0/13 | 0/13 | 1.0* | 1.0 | 1.1 | 3.7 |
| Heql/N2 | 26 | 0/26 | 26/26 | 1.6 | 8.7 | 6.4 | 6.7 |

*$\log_2$ of reciprocal of serum dilution at endpoint (titer means)
**Vaccine was administered at 0 and 36 days. The challenge with H3N2 was at 45 days.

None of the 39 subjects produced neutralizing antibodies to a recombinant containing only the hemagglutinin of the Hong Kong variant (i.e. H3N1). All subjects receiving Heql/N2 vaccine gave significant rises in NI antibody thus attesting to the specificity of the immunization. After infection with the challenge virus, NI antibody also appeared in the control group.

viral shedding, noted in earlier mouse studies, was not observed in the present studies in man.

TABLE III

Incidence and Severity of Illness in Control and Heq1/N2 Vaccine Groups

| Vaccine | No. of Subjects | Infected** | | Post-challenge events in those infected[+] | | | | | | | | | |
|---------|-----------------|------------|---|----|----|----|----|----|----|----|----|----|----|
| | | | | Ill | | URS | | Fever | | Sys. Symp. | | Virus Shed | |
| | | No. | % | No. | % | No. | % | No. | % | duration* | No. | % | % | dur.* |
| Control | 13 | 11 | (85) | 9 | (82) | 4 | (36) | 9 | (82) | 3.9 | 9 | (82) | (100) | 4.8 |
| Heq1/N2 | 26 | 15 | (58) | 5 | (33) | 5 | (33) | 3 | (20) | 3.3 | 2 | (13) | (84) | 4.8 |
| | | | | Post-challenge events (all subjects) | | | | | | | | | |
| Control | 13 | — | | 9 | (69) | 4 | (31) | 9 | (69) | 3.9 | 9 | (69) | (85) | 4.8 |
| Heq1/N2 | 26 | — | | 11 | (42) | 10 | (38) | 6 | (23) | 2.8 | 7 | (26) | (50) | 4.8 |

**number infected judged by 4-fold serologic response of virus isolation
URS = upper respiratory symptoms
Sys. = systemic symptoms
Symp.
*duration in days
[+]following exposure to H3N2 virus 9 days after second injection of vaccine The occurrence of influenza virus infection in the volunteers was assessed by serologic response by one or more of three different conventional tests (HI, neutralization or PI) or by recovery of virus during a period of 1–8 days after challenge with H3N2 virus. The HI test with H3N2 (Aichi) virus proved to be most sensitive and the PI test least sensitive at demonstrating antibody response (Table II below). Isolation of virus was closely concordant with serologic response shown by at least one test. Specifically, the ratios of positive serologic response/virus isolation were 10/11 in control subjects and 14/13 in X-32 vaccines (Table II). Eighty-five percent of control subjects, whereas only 50% of vaccines were shown to have been infected.

TABLE II

Serologic Evidence of Influenza Virus Infection in Vaccinated and Control Subjects Following Experimental Exposure to H3N2 (Hong Kong) Influenza Virus

| Vaccine Group | No. of Subjects | Significant (4-fold or >) Serologic Response by: | | | | | | | | | | Virus Isolation | |
|---------------|-----------------|------|------|------|------|------|------|------|------|----------|------|-----------------|------|
| | | HI | | Neut. | | PI | | NI | | any test | | | |
| | | No. | % | No. | % | No. | % | No. | % | No. | % | No. | % |
| Control | 13 | 8 | (62) | 9 | (69) | 3 | (23) | 8 | (62) | 10 | (77) | 11 | (85) |
| Heq1/N2 | 26 | 12 | (46) | 9 | (35) | 8 | (31) | 3 | (12) | 14 | (54) | 13 | (50) |

HI - hemagglutination-inhibition
NI - neuraminidase-inhibition
Neut. - neutralization
PI - plaque-inhibition Illness occurred in 82% of control and 33% of Heq1/N2 vaccinated subjects in whom laboratory evidence of influenza virus infection was present (see Table III below). While all such infection was attended by fever and systemic symptoms in controls (82%), only three of fifteen (20%) of vaccinated subjects in whom infection was demonstrated were febrile and only two had systemic reactions. The duration of fever and virus shedding was similar in both groups.

If the groups are examined in toto without reference to laboratory evidence of influenza virus infection (lower part of Table III) then the difference in illness rates in control and vaccinated groups lessens (69% vs. 42%, respectively) although again febrile illness is significantly reduced in vaccinated subjects. Significant protection against influenza could be obtained with 49% reduction of all illness and 62% reduction in febrile disease in those infected. The goal of obtaining infection uniformly in vaccinated subjects was partially realized, i.e., 58% compared with an incidence of 85% in controls. In contrast, previous studies in volunteers of conventional bi-specific vaccine, demonstrated serologic evidence of infection in only 14%. Reduction in The code named viruses used in forming the recombinant virus and vaccine of the present invention can be obtained from the Bureau of Biological Standards of the Food and Drug Administration.

A person of skill in the art upon reading the foregoing will become aware of a number of modifications which can be made to the invention described above without departing from the spirit and scope thereof. Hence, the foregoing is not to be taken as limiting since it is intended to be merely illustrative of a number of embodiments of the invention. The appended claims define the scope of protection sought.

I claim:

1. A method of influenza immunication comprising administering to a human or an animal subject to infection by natural means by naturally occurring influenza virus, by injecting an effective amount of a vaccine which comprises as an active ingredient, a recombinant, antigenically hybridized virus which contains a hemagglutinin antigen which has substantially no cross-reactivity with a challenge natural contemporaneous or naturally infective wild type influenza virus and a neuraminidase antigen which has substantial cross-reactivity with such a challenge influenza virus, said recombinant being derived from viruses which are not neurovirulent, the concentration of said virus in said vaccine being sufficient to immunize the human or animal.

2. A method, as claimed in claim 1, wherein the hemagglutinin antigen is derived from A/equine 1 virus.

3. A method, as claimed in claim 1, wherein the neuraminidase antigen is derived from an influenza virus selected from the group consisting of a subtype of Type A, B and C influenza viruses.

4. A method, as claimed in claim 1, wherein the neuraminidase antigen is derived from the Hong Kong variant of type A influenza virus.

5. A method, as claimed in claim 1, wherein the animal is man and the dosage that is administered is from about 500 to 1000 chick-cell agglutinating units.

6. A method of making a recombinant, antigenically hybridized virus, which comprises recombining a virus having a hemagglutinin antigen having substantially no cross-reactivity with a challenge influenza virus and an influenza virus having a neuraminidase antigen having substantial cross-reactivity with a challenge influenza virus, said viruses being nonneurovirulent, and thereafter immunizing a human or animal subject to naturally occurring influenza by injecting such human or animal with an effective amount of such vaccine.

7. A method according to claim 6 wherein the virus is derived by first recombining $A_o$ (H0N1) influenza virus with a Hong Kong variant of influenza to yield a progeny which is then recombined with A equine 1 virus.

8. A method described in claim 6 wherein the $A_o$ (H1N1) influenza virus is A./PR8/34 and the Hong Kong variant is HK/Aichi/68.

* * * * *

UNITED STATES PATENT OFFICE
CERTIFICATE OF CORRECTION

Patent No. 4,009,258          Dated February 22, 1977

Inventor(s) Edwin D. Kilbourne

It is certified that error appears in the above-identified patent and that said Letters Patent are hereby corrected as shown below:

Column 1, line 26, "in" should read -- is --;

Column 1, line 55, "monorather" should read -- mono- rather --;

Column 2, line 6, ", or man" should read -- or man, --;

Column 2, line 48, "A." should read -- $A_o$ --;

Column 4, line 28, after "product" insert -- was produced --;

Column 4, line 33, "uniactivated" should read -- uninactivated --;

Column 5, lines 1 and 2, delete in their entirety;

Column 5, line 11, "400" should read -- <400 --;

Column 5, line 40, "preformed" should read -- performed --;

Column 6, lines 45, 46 and 47, delete in their entirety;

Column 8, line 32, "immunication" should read -- immunization --;

UNITED STATES PATENT OFFICE
CERTIFICATE OF CORRECTION

Patent No. 4,009,258            Dated February 22, 1977

Inventor(s) Edwin D. Kilbourne

It is certified that error appears in the above-identified patent and that said Letters Patent are hereby corrected as shown below:

Column 10, line 9, "(H1N1)" should read -- (H0N1) --; and

Column 10, line 9, "A./PR8/34" should read -- $A_o$/PR8/34 --.

Signed and Sealed this

Seventh Day of June 1977

[SEAL]

Attest:

RUTH C. MASON
*Attesting Officer*

C. MARSHALL DANN
*Commissioner of Patents and Trademarks*